United States Patent [19]
Mardente et al.

[11] Patent Number: 5,514,365
[45] Date of Patent: May 7, 1996

[54] PHARMACEUTICAL COMPOSITIONS COMPRISING CALCITONIN FOR INTRANASAL ADMINISTRATION

[75] Inventors: Salvatore Mardente; Rodolfo Corneli; Marilena Carazzone, all of Milan, Italy

[73] Assignee: Schiapparelli Salute S.P.A., Milan, Italy

[21] Appl. No.: 232,471

[22] Filed: Apr. 25, 1994

Related U.S. Application Data

[63] Continuation of Ser. No. 144,995, Oct. 29, 1993, abandoned, which is a continuation of Ser. No. 663,838, May 8, 1991, abandoned.

[30] Foreign Application Priority Data

Oct. 11, 1988 [IT] Italy ........................... 22257/88
Nov. 8, 1988 [IT] Italy ........................... 22548/88

[51] Int. Cl.⁶ ........................... A61K 9/12; A61K 38/23
[52] U.S. Cl. ........................... 424/45; 424/43; 514/958; 514/970; 514/808
[58] Field of Search ........................... 424/45, 43; 514/808, 514/958, 970

[56] References Cited

FOREIGN PATENT DOCUMENTS

| 2127689 | 4/1984 | European Pat. Off. . |
| 115627 | 8/1984 | European Pat. Off. . |
| 0156772 | 10/1985 | European Pat. Off. . |
| 01933782 | 9/1986 | European Pat. Off. . |

OTHER PUBLICATIONS

Ganong. (1987). Review of Medical Physiology. Appleton S Lange, pp. 329–331.
Gennaro. (1985). Remington's Pharmaecutical Sciences, Mack Pub., p. 979.

*Primary Examiner*—Thurman K. Page
*Assistant Examiner*—Raj Bawa
*Attorney, Agent, or Firm*—Walter H. Schneider

[57] ABSTRACT

A method for treating a patient suffering from any of osteoporosis, Paget's disease and hypercalcemia by intranasally administering to said patient by spray a calcitonin solution consisting of calcitonin dissolved in a 0.9% aqueous sodium chloride solution free of quaternary ammonium compounds and surfactants, the calcitonin being in a concentration of 100–5000 IU per ml. of composition.

4 Claims, No Drawings

PHARMACEUTICAL COMPOSITIONS COMPRISING CALCITONIN FOR INTRANASAL ADMINISTRATION

CROSS-REFERENCES TO RELATED APPLICATIONS

This application is a continuation of Appl. Ser. No. 08/144,995 filed Oct. 29, 1993, now abandoned, which is a continuation of Appl. Ser. No. 07/663,838 filed May 8, 1991, now abandoned.

BACKGROUND OF THE INVENTION

1. Field of the Invention

The present invention relates to pharmaceutical compositions comprising calcitonin and to a spray unit for the intranasal administration of said compositions.

More particularly, the invention relates to pharmaceutical compositions whose active ingredient is calcitonin, which compositions are free from preservants and surfactants.

Still more particularly, the invention relates to pharmaceutical compositions for intranasal administration, comprising calcitonin—preferably salmon calcitonin—dissolved in physiological saline adjusted to pH 3.5–4.5 by means of hydrochloric acid.

2. Description of the Prior Art

Calcitonins are known to be of basic importance in the treatment of osteoporosis, Paget's disease, hypercalcemia and similar pathological conditions. Calcitonins are also known to undergo degradation easily, due to the polypeptide nature thereof; as a consequence, they cannot be administered by the oral route. On the other hand, parenteral administration of calcitonins by injection involves remarkable disadvantages, particularly painful reactions in the patient.

Intranasal administration of polypeptide drugs is also widely described in literature; see, e.g., Felber et al., *Experientia*, 1969, page 1195; Gennser et al., *Lancet*, 1974, page 865; Greenberg et al., *Antimicrobial Agents and Chemotherapy*, 1978, page 596; Bergquist et al., *Lancet*, 1979, page 215; Pontiroli et al., *British Medical Journal*, 1982, page 303, besides a number of patents or patent applications concerning intranasal administrations of insulin (EP 94157), vasopressin (Japanese Patent applications 55066-517, 55055-120), polypeptides of various nature (German Patents 2.256.445 and 2.758.483, EP 252, Belgian Patent 860.717, South African Patent 68/4241).

Intranasal administration of calcitonin is in its turn disclosed in various patents. Thus, Italian Patent 1.172.324 claims galenic compositions comprising calcitonin characterized in that they contain, besides the active ingredient, benzalkonium chloride or a surfactant, particularly a non-ionic surfactant, or both the above additives. Higher alkanols or sterol polyoxyalkylene ethers are particularly claimed as surfactants.

Both surfactants and benzalkonium chloride are indicated to be necessary ingredients to provide a good calcitonin bioavailability, that is to assure the effective adsorption thereof by nasal mucosa, while benzalkonium chloride would also act as a preservant against pathogen or undesirable micro-organisms.

Similar compositions containing a quaternary ammonary salt (benzalkonium chloride, cetyltrimethylammonium bromide) are claimed in EP-A-193.372. Japanese Patent Application 61126-034 discloses nasal formulations of calcitonin containing absorption-increasing agents such as glucose and/or glucosamine. The need for an absorption adjuvant is also stressed by Japanese Patent Application 61118-325, which proposes for this purpose the addition of amino acids, and by EP-A-183.527, which suggests the use of benzyl alcohol, ethanol, salicylic acid, capronic acid, polyethylene glycol and the like as absorption enhancers. Moreover, EP-A-111.841 and EP-A-115.627 claim intranasal compositions containing calcitonin in admixture with surfactants, among which biliary acids and benzalkonium chloride are disclosed.

Nevertheless, the presence of the latter—and generally of quaternary ammonium salts—is not satisfactory due to the possible undesired effects thereof; see, e.g., Am. J. Ophthalmol., Jun. 15, 1988, vol. 105 (6), pp. 670–3; Contact Dermatitas, July 1987, vol. 17 (1), pp 41–2; and Cutis, May 1987, vol.39 (5), pp. 381–3. Therefore, it would seem to be better to provide intranasal compositions of calcitonin free from said salts. However, according to some of the above mentioned documents, said compositions would suffer from poor bioavailability.

All the patent documents reported above completely agree on the need to enhance said bioavailability by means of surfactants of various natures which promote calcitonin absorption through nasal mucosa.

SUMMARY OF THE INVENTION

Therefore, it is really surprising that intrasal compositions of calcitonin containing surfactants, or agents intended to increase absorption by the nasal mucosa, and compositions containing calcitonin alone in a substantially physiological aqueous solution of sodium chloride, practically show no differences in bioavailability nor in preservability.

Therefore, an object of the present invention is provided by pharmaceutical formulations for intranasal administration comprising:

a) a therapeutically effective amount of calcitonin, dissolved in b) a 0.9% NaCl solution in purified water adjusted to pH 3.5–4.5.

Preferably, according to the invention, the compositions consist of:

a) a therapeutically effective amount of salmon calcitonin dissolved in b) a 0.9% NaCl solution in purified water, adjusted to pH 3.5–4.5 by means of hydrochloric acid.

Moreover, the compositions according to the invention preferably contain 100 to 5.000 I.U., advantageously 250 to 2,000 I.U., of calcitonin per ml of composition.

The advantage of the composition of this invention is that quaternary ammonium salts as well as calcitonin absorption enhancing agents are both avoided.

DESCRIPTION OF THE PREFERRED EMBODIMENT

The composition of the invention was compared with compositions prepared according to the prior art, particularly the pharmaco-kinetic following intranasal administration of the same dosages (100 I.U.) of salmon calcitonin (salcatonin) in the formulations A and B, in 12 subjects each time:

| A) Salcatonin | I.U. | 100 |

-continued

|   |   |   |   |
|---|---|---|---|
| Sodium chloride | mg | 0.9 |
| 1N hydrochloric acid, q. s. to | pH | 4.0 |
| Purified water, q. s. to | ml | 0.1 |
| B) Salcatonin | U.I. | 100 |
| benzalkonium chloride | mg | 0.0091 |
| 1N hydrochloric | mg | 0.77 |
| Purified water, q. s.. to | pH | 4.0 |
| Treatment | ml | 0.1 |

Salcatonin plasma concentrations (12 subject mean ± standard error) at various times from administration, are reported in the following Table:

| Minutes | A (pc/ml) | B (pc/ml) |
|---|---|---|
| 0 | 0 | 0 |
| 5 | 25 | 25 |
| 10 | 52 | 55 |
| 20 | 68 | 72 |
| 30 | 38 | 45 |
| 40 | 22 | 20 |
| 50 | 15 | 12 |
| 60 | 10 | 5 |
| 120 | 0 | 0 |

The AUC (area under curve) is 1663 in case of A and 2108 in case of B. $T/2\beta$ is 12.2 minutes and 11.7 minutes, respectively.

The difference between the two curve types is not significant.

Completely analogous results are obtained by comparing the compositions of the invention with compositions containing, instead of benzalkonium chloride, a cholesterol polyoxyethylene ether or respectively ethanol, salicylic acid and sodium taurocholate.

The following non limiting examples illustrate the invention in more detail.

EXAMPLE 1

Salcatonin (500,000 I.U.) is dissolved in 850 ml of depurated water containing 9 g of analytically pure sodium chloride;pH is adjusted to 4.0 by means of analytically pure 1N HCl and the solution is diluted to 1.000 ml by adding purified water. The solution is filtered on a 0.2 um filter and distributed in 5 ml containers as disclosed in the annexed figures, provided with a doser delivering 0.1 ml doses each time, equal to 50 I.U. of salcatonin.

EXAMPLE 2

The procedure of example 1 is followed, but using a double amount of salcatonin (1,000.000 I.U.). The solution is distributed in suitable 2.5 ml containers as disclosed in the annexed figures delivering 0.1 ml doses each time, equal to 100 U.I. of salcatonin.

We claim:

1. A method for treating a patient suffering from any of osteoporosis, Paget's disease and hypercalcemia which comprises intranasally administering by spray to said patient a dosage of a liquid composition consisting of a therapeutically effective amount of calcitonin dissolved in an 0.9% aqueous chloride solution free of quaternary ammonium compounds and surfactants and adjusted to a pH of 3.5–4.5, the concentration of calcitonin being 100–5000 IU per ml. of composition.

2. A method according to claim 1 in which the dosage is about 100 microliters.

3. A method according to claim 1 in which the concentration is about 250–2000 I.U. per ml. of composition.

4. A method according to claim 1 in which the calcitonin is salmon calcitonin.

* * * * *